United States Patent
Aleksandrovich et al.

(10) Patent No.: US 10,603,302 B2
(45) Date of Patent: Mar. 31, 2020

(54) WATER SOLUBLE FLAVONOIDS

(71) Applicants: Roman Aleksandrovich, Brooklyn, NY (US); Oleg Ponomarev, Englishtown, NJ (US)

(72) Inventors: Roman Aleksandrovich, Brooklyn, NY (US); Oleg Ponomarev, Englishtown, NJ (US)

( * ) Notice: Subject to any disclaimer, the term of this patent is extended or adjusted under 35 U.S.C. 154(b) by 0 days.

(21) Appl. No.: 16/104,466

(22) Filed: Aug. 17, 2018

(65) Prior Publication Data

US 2019/0060272 A1 Feb. 28, 2019

Related U.S. Application Data

(60) Provisional application No. 62/549,168, filed on Aug. 23, 2017.

(51) Int. Cl.
| | |
|---|---|
| *A61K 31/353* | (2006.01) |
| *A61K 47/12* | (2006.01) |
| *A61K 47/18* | (2017.01) |
| *A61K 9/14* | (2006.01) |
| *A61K 9/00* | (2006.01) |
| *A61K 9/08* | (2006.01) |

(52) U.S. Cl.
CPC .......... *A61K 31/353* (2013.01); *A61K 9/0095* (2013.01); *A61K 9/08* (2013.01); *A61K 9/145* (2013.01); *A61K 47/12* (2013.01); *A61K 47/183* (2013.01)

(58) Field of Classification Search
None
See application file for complete search history.

(56) References Cited

FOREIGN PATENT DOCUMENTS

WO  WO-2011049629 A9 * 5/2012 ............. A61K 8/498

OTHER PUBLICATIONS

English Translation of RU 2545905, Published Apr. 10, 2015 (Year: 2015).*

* cited by examiner

*Primary Examiner* — Jeffrey S Lundgren
*Assistant Examiner* — William Y Lee
(74) *Attorney, Agent, or Firm* — Aleksandr Smushkovich

(57) ABSTRACT

Methods for obtaining a stable solution to enhance bioavailability of flavonoids (e.g. Taxifolin/Dihydromericetine, or Quercetin) include the following steps:
  mixing, in predetermined amount, the flavonoid with Citric acid, obtaining a first mixture,
  grinding the first mixture for 10-15 minutes,
  mixing the first mixture with a predetermined amount of L-Arginine, obtaining a second mixture,
  grinding the second mixture for 15 minutes, and either
  adding water to the second mixture, thereby obtaining the stable solution, or
  storing the second mixture for further use. Exemplarily, there are disclosed specific weight amounts for each ingredient of the solution.

3 Claims, 1 Drawing Sheet

WATER SOLUBLE FLAVONOIDS

CROSS REFERENCES TO RELATED APPLICATIONS

The present patent application claims the benefit of a U.S. provisional patent application Ser. No. 62/549,168 filed on Aug. 23, 2017, the disclosure of which is incorporated herein in its entirety by reference.

FIELD OF THE INVENTION

The invention relates to organic chemistry of bioactive flavonoids with antioxidant properties, especially to a new stable water soluble form with enhanced bioavailability. In particular, the invention relates to creating a new procedure for the formulation of stable water soluble forms of bioflavonoids.

BACKGROUND OF THE INVENTION

Taxifolin (5,7,31,41-tetrahydroxyflavanol,dihydroquercetin) is a member of the flavonoid family. Moleculars of a similar structure to Taxifolin (such as Quertsetin, Myricetin, Dihydromyricetin, Catechin) elicit a wide range of pharmacological effects of anti-oxidation and anti-radiation [1.2] (see [References] herein below).

Furthermore, all mentioned flavonoids also have anti-inflammation activity, anti-viral activity, anti-tumor activity, and protective postmenopausal osteoporosis activity [3-6]. Due to its pharmacological diversity, its bioavailability and biological properties have raised a great interest for future studies [7-8].

Flavonoids, including Taxifolin, are slightly soluble in water and show a slow dissolution rate from solid oral dosage forms, restricting their clinical use. The poor solubility of active pharmaceutical ingredients in water and their low dissolution rate in the aqueous gastro-intestinal fluids often leads to insufficient bioavailability; which becomes one of the most difficult problems in pharmaceutical and food supplement technology.

The dissolution of poor water-soluble drugs that undergo rate-limited gastrointestinal absorption can generally be improved with many techniques, one of which is the preparation of nanodispersion [8-10]. This technology provides the possibility of reducing the drug particle size. With polyvinylpyrrolidone (PVP) selected as the carrier, this increases the surface area and hence, improves the dissolution rates [11,12].

An alternative way to increase solubility is by using the polyglycol molecules[13] or infusion complexes with Cyclodextrines[14].

The analysis of the data leads to the conclusion that existing methods and approaches for improving solubility in water, or for creating completely water-soluble compositions, have many limitations and do not yet lead to their widespread use in the creation of new effective pharmaceutical preparations or water-soluble food additives.

The use of polyglycols to increase solubility in water or a high concentration of cyclodextrins is in some cases unacceptable for the final product. In addition, instability of the complexes leads to the possibility of crystallization of said insoluble product, just as the use of heating and using solvents in their preparation acts in the same manner.

An attempt to create a water soluble composition was done with a combination of Taxifolin and Rutine with a glycoside group in the structure. That mixture is achieved in solution only by heating to 60 degrees Celsius, and the data of such complex stability is missing.

In patents [16] a water soluble composition was prepared with mixing Taxifolin and L-arginine in an Argon atmosphere, which illustrates the instability of such mixture. Data about stabilization of water solution is also missing. The same drawback is seen in patent [17], that uses a mixture of flavonoids including Taxifolin as a part of Silybum Marianum, a mixture of basic amino acids (including L-arginine), polyols and amorphous Mg/Al metasilicate that helps formulation.

Thus, the use of new approaches for the creation of stable water-soluble bioflavonoids and their subsequent application in the development of new effective pharmaceuticals and food additives is still in high demand.

Examples of such approaches follow ([References]):

1. Sun, X.; Chen, R. C.; Yang, Z. H.; Sun, G. B.; Wang, M.; Ma, X. J.; Yang, L. J.; Sun, X. B. Taxifolin prevents diabetic cardiomyopathy in vivo and in vitro by inhibition of oxidative stress and cell apoptosis. Food Chem. Toxicol. 2013, 63, 221-232. [Cross Ref] [Pub Med].

2. Tiukavkina, N. A.; Rulenko, I. A.; Kolesnik, I. U. A. Dihydroquercetin-anewantioxidantandbiologicallyactive food sdditive. J. Vopr. Pitan. 1997, 6, 12-15.

3. Oi, N.; Chen, H. Y.; Kim, M. O.; Lubet, R. A.; Bode, A. M.; Dong, Z. G. Taxifolin suppresses UV-induced skin carcinogenesis by targeting EGFR and PI3K. Cancer Prey. Res. 2012, 5, 1103-1114. [Cross Ref] [Pub Med]

4. Satue, M.; Arriero, M. M.; Monjo, M.; Ramis, J. M. Quercitrin and taxifolin stimulate osteoblast differentiation in MC3T3-E1cellsandinhibitosteoclastogenesisinRAW264.7cells. Biochem. Pharmacol. 2013, 86, 1476-1486. [Cross Ref] [Pub Med]

5. Tamara, V. A.; Antonina, F. K.; Ludmila, N. K.; Maria, K. L.; Vera, V. S.; Yuri, N. K. Effects of taxifolin on the activity of angiotensin-converting enzyme and reactive oxygen and nitrogen species in the aorta of aging rats and rats treated with the nitric oxide synthase. Age 2013, 35, 2089-2097.

6. Verma, S.; Singh, A.; Mishra, A. Dual inhibition of chaperoning process by taxifolin: Molecular dynamics imulation study. J. Mol. Graph. Model. 2012, 37, 27-38. [Cross Ref] [Pub Med].

7. UHPLC-MS/MS Determination, Pharmacokinetic, and Bioavailability Study of Taxifolin in Rat Plasma after Oral Administration of its Nanodispersion Chun-Juan Yang 1, Zhi-Bin Wang 2,*, Ying-Ying Mi 2, Ming-Jie Gao 1, Jin-Nan Lv 2, Yong-Hai Meng 2, Bing-You Yang 2 and Hai-Xue Kuang 2,* 1 College of Pharmacy, Harbin Medical University, No. 157 Baojian Road, Nangang District, Harbin 150081, Heilongjang, China; chunjuanyang@126.com (C.-J. Y.); gaomingjie8888@163.com (M.-J. G.) 2 Key Laboratory of Chinese Materia Medica (Ministry of Education), Heilongjiang University of Chinese Medicine, Harbin 150040, Heilongjang, China; ccmini731@163.com (Y.-Y. M.); liyufeng5211314@126.com (J.-N. L.); 15845002546@139.com (Y.-H. M.); ybywater@163.com (B.-Y. Y.)*Correspondence: wzbmailbox@126.com (Z.-B. W.); hxkuang@yahoo.com (H.-X. K.); Tel./Fax: +86-451-8726-6862 (Z.-B. W. & H.-X. K.) Academic Editor: Derek J. McPhee Received: 6 Mar. 2016; Accepted: 11 Apr. 2016; Published: 14 Apr. 2016

8. Published in final edited form as: J Neurosci. 2012 Jan. 4; 32(1): 390-401

9. Kallay, N.; Zalac, S. Stability of nanodispersions: A model for kinetics of aggregation of nanoparticles. J. Colloid Interface Sci. 2002, 25, 70-76. [Cross Ref] [Pub Med]

10. Nkansah, P.; Antipas, A.; Lu, Y.; Varma, M.; Rotter, C.; Rago, B.; El-Kattan, A.; Taylor, G.; Rubio, M.; Litchfield, J. Development and evaluation of novel solid nanodispersion system for oral delivery of poorly water-soluble drugs. J. Control. Release 2013, 169, 150-161. [Cross Ref] [Pub Med]

11. Tam, J. M.; Mcconville, J. T.; Williams, R. O., III; Johnston, K. P. Amorphous cyclosporin nanodispersions for enhanced pulmonary deposition and dissolution. J. Pharm. Sci. 2008, 97, 4915-4933. [Pub Med]

12. Constantinides, P. P.; Chaubal, M. V.; Shorr, R. Advances in lipid nanodispersions for parenteral drugdelivery and targeting. Adv. Drug. Deliv. Rev. 2008, 60, 757-767. [Cross Ref] [Pub Med]

13. Shikov, A. N.; Pozharitskaya, O. N.; Sabiruddin Mirza, I. M.; Urakovalrina, N.; Hirsjarvi, S.; Makarov, V. G.; Heinamaki, J.; Yliruusi, J.; Hiltunenc, R. Nanodispersions of taxifolin: Impact of solid-state propertieson dissolution behavior. Int. J. Pharm. 2009, 377, 148-152. [Cross Ref] [Pub Med]

14. Formulation of microencapsulated food ingredients for fat containing products. Patentpak by
Bazarova Yu. G, Moskalev E. V, Andreeva N. Yu; Bazarova A. V. From Russ. (2009). Language:Russian, Database CAPLUS 15. Asian Journal of Pharmaceutical sciences 9(2014) 304-3166

16. Water soluble flavonoid composition, and foods, beverages, and cosmetics containing them. Patentpak. By Hashizume, Yujiz Takado, Taketoshi; Iida, Junji From Jpn. Kokai Tokkyo Koho (2008), JP 2008092869 A Apr. 24, 2008/Language: Japanese, Database: CAPSUL 17. Water soluble pharmaceutical composition L-arginine-Dihydroqurcetin and method of obtaining thereof. Patentpak.
By Koroteev A. M; Kaziev G. Z., Koroteev M. P., Zinchenko V. P, Teleshev A. T., Perepelkin M. V. From Russ. (2015), RU 2545905 C1 Apr. 10, 2015/language: Russian, Database: CAPLUS 18. Water-soluble formulation based on flavanol lignans and process for their preparation.
PATENTPAK By Stuchlik, Milan; Kopenec, Jiri From Czech Rep. (2009), CZ 300846 B6 Aug. 26, 2009./language: Czech, Database: CAPLUS

OBJECT AND BRIEF SUMMARY OF THE INVENTION

Therefore, a primary object of the present invention is the obtaining of a new stable water soluble formula that will enhance bioavailability of the natural flavonoid (e.g. Taxifolin, or Dihydromericetine, or Quercetin) and products with a similar structure widely used in cosmetic and pharmaceutical formulations and food supplement products.

The inventive methods for obtaining a stable solution to enhance bioavailability of flavonoids (e.g. Taxifolin, or Dihydromericetine, or Quercetin) comprise the following steps: —mixing, in predetermined amount, the flavonoid with Citric acid, obtaining a first mixture; —grinding the first mixture for 10-15 minutes; —mixing the first mixture with a predetermined amount of L-Arginine, obtaining a second mixture; 13 grinding the second mixture for 15 minutes; and either 13 adding water to the second mixture, thereby obtaining the stable solution; or 13 storing the second mixture for further use. Exemplarily, there are disclosed specific weight amounts for each ingredient of the solution.

DRAWINGS OF THE INVENTION

The present invention is illustrated in the attached drawings.

DETAIL DESCRIPTION OF THE INVENTION

Figure 1:
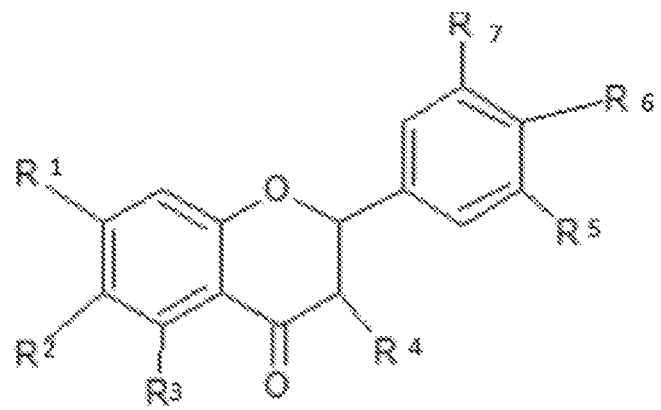
FIG. 1 shows a chemical structure of Taxifolin/Dihydroquercetin and its analogues wherein: R1=R3=R4=R6=R7=OH, R2=R5=H; R2=H, R1=R3=R4=R6=R7=OH, according to an embodiment of the invention.

While the invention may be susceptible to embodiment in different forms, there are shown in the drawings, and will be described in detail herein, specific embodiments of the present invention, with the understanding that the present disclosure is to be considered an exemplification of the principles of the invention, and is not intended to limit the invention to that as illustrated and described herein.

Figure 2:
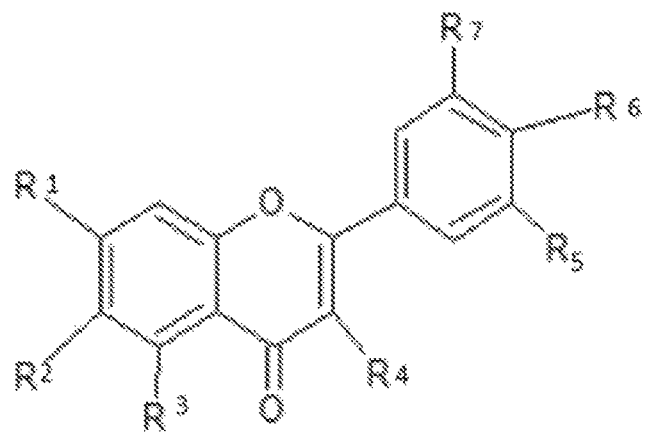
FIG. 2 shows a chemical structure of Quercetin and its analogues wherein: R1=R3=R4=R6=R7=OH, R2=R5=H; R2=H, R1=R3=R4=R6=R7=OH, according to another embodiment of the invention.
Figure 3:
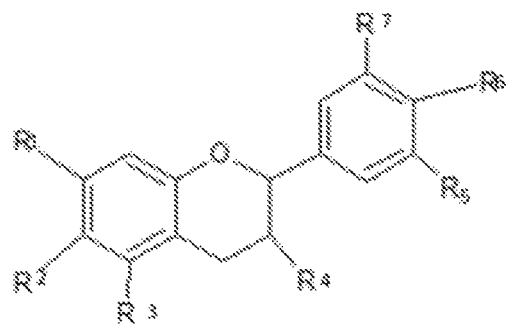
FIG. 3 shows a chemical structure wherein: R2=R5=H, R1=R3=R6=R7=OH, R4=O-diglucoside, according to another embodiment of the invention.

The above stated object has been achieved in the present invention by providing a formulation using mechanical grinding of any of the flavonoids with antioxidant properties, illustrated in FIGS. 1-3, and L-Arginine amino acid with Citric acid at room temperature. Stability of the resultant water solution was achieved by using Citric acid in certain proportions that acts like a pH stabilizer and preservative.

L-Arginine, as a basic amino acid, forms a complex with A-benzole ring hydroxyl group with partial proton dissociation that was control by electronic absorption spectra. Without Citric acid in a mixture of Taxifolin and L-Arginine, the mixture gets red coloration in a solid form and water solution; this color is time-dependent getting deeper in 10-15 minutes.

The formation of a colored tautimeric form with indeterminate properties caused the need to stabilize the pH of the solution and prevent this process. The authors discovered that stabilization of a solid mixture of Taxifolin/Dihydromericetine (or Quercetin) and L-Arginine was achieved with Citric acid that gave a clear water solution with stable spectral and physical properties for more than 2 months. Citric acid also acts as a preservative for the solid mixture and water solution.

The following examples illustrate some preferred embodiments of the invention:

EXAMPLE 1

Taxifolin/Dihydroquercetin (96.8% purity) 5 g was mixed and grinded with Citric acid 2 g on a roller mill for 10-15 minutes, and after that L-Arginine 2 g was added to the mixture and continue grinded 15 minutes more. The mixture was transferred to a closed container and ready to use for a water solution or solid ingredients formulation. 400 mg of this mixture can be dissolve in 150 ml of water instantly, and form a clear stable solution.

EXAMPLE 2

Quercetin (98.3% purity) 5 g was mixed and grinded with Citric acid 2 g on a roller mill for 10-15 minutes, and after that L-Arginine 2 g was added to the mixture and continued grinding for 15 minutes more. The mixture was transferred to a closed container and ready to use for a water solution or solid ingredients formulation. 400 mg of this mixture can be dissolved in 150 ml of water instantly, forming a clear stable solution.

These two examples above can be used for preparation of any other structures of water soluble flavonoids above shown in FIG. 13, and used in pharmaceutical, cosmetic products and food additives with increased bioavailability.

EXAMPLE 3

The product from Example 1 (as well as the products from Example 2) was taken in an amount of 9 g, to which product 2.2 g of Succinic acid and 2 g of Ascorbic acid were added. The so obtained mixture was mixed on and grinded by a roller mill for 10-15 minutes. The resultant mixture was transferred to a closed container and ready to use for a water solution or solid ingredients formulation. 400 mg of this mixture is added to 150 ml of water that instantly forms a clear stable solution.

The above described products can be used as food additives and help protecting a human's brain and liver from Ethyl alcohol intoxication, due to its solubility in water, which increases bioavailability, and also for water formulated juices, lemonades, etc.

The claimed invention is:

1. A method for obtaining a stable solution to enhance bioavailability of Taxifolin; said method comprising the steps of:
   a) mixing an amount of Taxifolin with an amount of Citric acid in air atmosphere, obtaining a first mixture;
   b) grinding the first mixture for 10-15 minutes;
   c) mixing the first mixture with an amount of L-Arginine, obtaining a second mixture;
   d) grinding the second mixture for 15 minutes; and
   e) adding an amount of water to the second mixture, thereby obtaining said stable solution.

2. The method according to claim 1, wherein:
   said Taxifolin has a purity of 96.8%;
   said amount of Taxifolin is 5 g;
   said amount of Citric acid is 2 g;
   said amount of L-Arginine is 2 g; and
   said amount of water is equal to $3/8$ of a weight of the second mixture.

3. A method for obtaining a stable solution to enhance bioavailability of Taxifolin; said method comprising the steps of:
   a) mixing an amount of Taxifolin with an amount of Citric acid in air atmosphere, obtaining a first mixture;
   b) grinding the first mixture for 10-15 minutes;
   c) mixing the first mixture with an amount of L-Arginine, obtaining a second mixture;
   d) grinding the second mixture for 15 minutes; and
   e) storing the second mixture for further use.

* * * * *